US008536393B2

(12) United States Patent
Evans et al.

(10) Patent No.: US 8,536,393 B2
(45) Date of Patent: Sep. 17, 2013

(54) INTEGRATED PROCESS TO PRODUCE C4+ HYDROCARBONS WITH REMOVAL OF BROMINATED ORGANIC IMPURITIES

(75) Inventors: Wayne Errol Evans, Richmond, TX (US); Glenn Charles Komplin, Katy, TX (US); Duraisamy Muthusamy, Houston, TX (US)

(73) Assignee: Shell Oil Company, Houston, TX (US)

( * ) Notice: Subject to any disclaimer, the term of this patent is extended or adjusted under 35 U.S.C. 154(b) by 119 days.

(21) Appl. No.: 13/319,748

(22) PCT Filed: May 11, 2010

(86) PCT No.: PCT/US2010/034333
§ 371 (c)(1),
(2), (4) Date: Nov. 10, 2011

(87) PCT Pub. No.: WO2010/132409
PCT Pub. Date: Nov. 18, 2010

(65) Prior Publication Data
US 2012/0053381 A1 Mar. 1, 2012

Related U.S. Application Data

(60) Provisional application No. 61/177,692, filed on May 13, 2009.

(51) Int. Cl.
*C07C 1/00* (2006.01)
*C07C 2/00* (2006.01)

(52) U.S. Cl.
USPC ........... 585/359; 585/943; 585/408; 585/310; 585/469; 585/642; 585/422; 585/733; 585/820; 208/262.1

(58) Field of Classification Search
None
See application file for complete search history.

(56) References Cited

U.S. PATENT DOCUMENTS

| 3,935,289 | A | 1/1976 | de Radzitzky d'Ostrowick et al. ............... 260/660 |
| 4,747,937 | A * | 5/1988 | Hilfman et al. ........... 208/251 R |
| 4,952,746 | A * | 8/1990 | Johnson et al. ............... 585/802 |
| 4,971,664 | A | 11/1990 | Turro et al. ............... 204/158.12 |
| 6,525,230 | B2 | 2/2003 | Grosso ............... 568/891 |
| 7,244,867 | B2 | 7/2007 | Waycuilis ............... 585/408 |
| 8,105,481 | B2 * | 1/2012 | Driver et al. ............... 208/262.1 |
| 8,273,929 | B2 * | 9/2012 | Stoimenov et al. ........... 585/310 |
| 2005/0038310 | A1 | 2/2005 | Lorkovic et al. ............. 585/943 |
| 2005/0171393 | A1 | 8/2005 | Lorkovic ............... 585/357 |
| 2007/0238909 | A1 | 10/2007 | Gadewar et al. ............... 585/16 |
| 2010/0234637 | A1* | 9/2010 | Fong et al. ............... 562/412 |

* cited by examiner

*Primary Examiner* — Tam M Nguyen

(57) ABSTRACT

The present invention provides an integrated process for producing aromatic hydrocarbons and/or C4+ non-aromatic hydrocarbons from low molecular weight alkanes, which includes contacting the low molecular weight alkanes with a halogen and coupling the monohaloalkanes to form aromatic hydrocarbons and/or C4+ non-aromatic hydrocarbons.

8 Claims, 1 Drawing Sheet

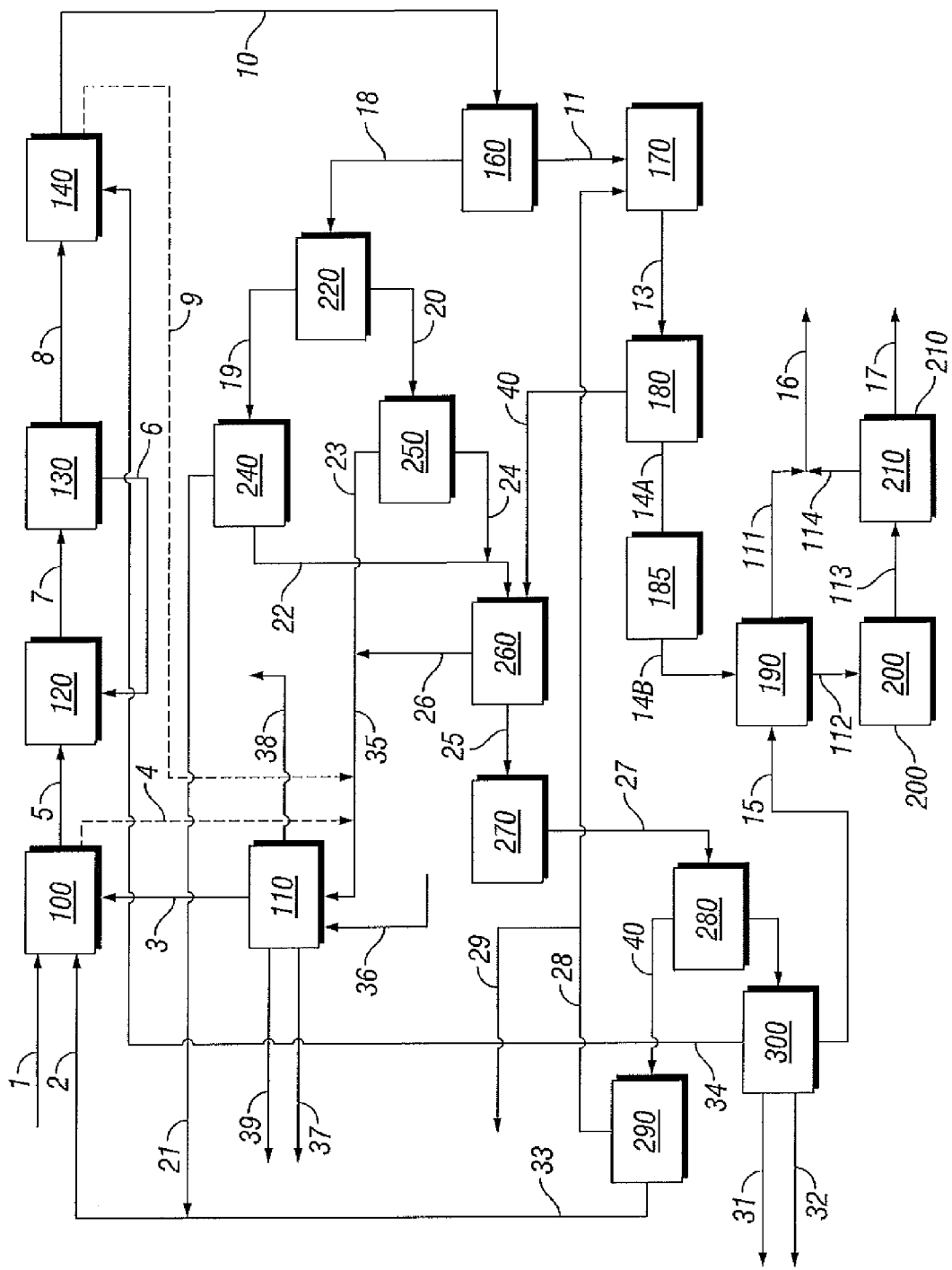

INTEGRATED PROCESS TO PRODUCE C4+ HYDROCARBONS WITH REMOVAL OF BROMINATED ORGANIC IMPURITIES

PRIORITY CLAIM

The present application is a 371 application of PCT/US2010/034333 and claims priority from PCT/US2010/034333, filed 11 May 2010, which claims priority from U.S. provisional application no. 61/177,692, filed 13 May 2009, which is incorporated herein by reference.

FIELD OF THE INVENTION

This invention relates to an improved process for the production of C4+ hydrocarbons by bromination of low molecular weight alkanes, particularly methane. More particularly, the invention relates to such a process wherein brominated organic impurities are removed from hydrocarbon streams.

BACKGROUND OF THE INVENTION

U.S. Pat. No. 7,244,867 describes a process for converting lower molecular weight alkanes, including methane, natural gas or ethane, propane, etc., into higher molecular weight hydrocarbons, including aromatics, by bromination to form alkyl bromides and hydrobromic acid which are then reacted over a crystalline alumino-silicate catalyst to form the higher molecular weight hydrocarbons and hydrobromic acid. Hydrobromic acid is recovered by contacting the reaction product stream with water and then converted to bromine for recycle. The higher molecular weight hydrocarbons are recovered.

In a process for producing aromatic hydrocarbons such as benzene, toluene and/or xylenes (BTX) and/or $C_{4+}$ nonaromatic hydrocarbons by bromination of methane to produce monobromomethane, followed by coupling of the monobromomethane to produce the desired hydrocarbons, the coupling reactor produces hydrogen bromide (HBr), and unintended amounts of methane, light ends ($C_{2-3}$ alkanes and alkenes) and heavy ends ($C_{9+}$ aromatic hydrocarbons). The basic process concept may include recycle of the light ends, possibly to a separate bromination reactor, and the use of methane and heavy ends as fuel.

Methane present in natural gas may be brominated by a high temperature reaction with elemental bromine to produce brominated products consisting primarily of methyl bromide and hydrogen bromide (HBr). In separation steps, HBr may be recovered for bromine regeneration, poly bromides recovered for recycle, and methyl bromide recovered. In the second reaction step, methyl bromide may be passed over a catalyst at high temperature to carry out a coupling reaction that yields a product mixture containing aromatic and aliphatic compounds and HBr. Alternately, in the second reaction step the entire stream from the bromination step is employed. Product separation steps are employed to recover the HBr byproduct and to separate the organic products into light hydrocarbons, $C_{4+}$ non-aromatic hydrocarbons, aromatics and heavy ends. Brominated organic compounds are present as undesirable impurities in the organic product streams. While organic bromides (even methyl bromides) can be separated from $C_{1-3}$ hydrocarbons simply by distillation, these impurities are very difficult to remove from aromatic hydrocarbons and $C_{4+}$ non-aromatic hydrocarbons by conventional techniques such as distillation or selective absorption.

Very stringent product specifications must be met with respect to halogenated impurities in the finished product. Undesirable refractory (difficult to remove) brominated organic impurities are often present in the hydrocarbon product streams.

It can be seen that it would be advantageous to provide an integrated process concept wherein undesirable brominated organic impurities could be removed or converted into hydrocarbons, possibly for recycle, to greatly reduce the total amount of brominated organic impurities that must be disposed of. The present invention provides such an integrated process.

SUMMARY OF THE INVENTION

The present invention provides an integrated process for producing aromatic hydrocarbons and/or $C_{4+}$ non-aromatic hydrocarbons from low molecular weight alkanes, preferably methane, which comprises:

(a) contacting one or more low molecular weight alkanes, preferably methane, with a halogen, preferably bromine, under process conditions sufficient to produce a monohaloalkane, preferably monobromomethane, (b) reacting the monohaloalkane in the presence of a coupling catalyst to produce a stream comprising aromatic hydrocarbons and/or $C_{4+}$ non-aromatic hydrocarbons and halogenated organic impurities, (c) hydrotreating the stream from step (b) under conditions sufficient to convert most of said impurities to hydrogen halide, preferably hydrogen bromide (HBr), and hydrocarbons while minimizing the hydrogenation of the aromatic hydrocarbons, to produce a stream comprising aromatic hydrocarbons and/or $C_{4+}$ non-aromatic hydrocarbons and refractory halogenated organic impurities, (d) contacting the stream from step (c) with a purification absorbent capable of reducing the quantity of said refractory halogenated organic impurities in said stream from (c), preferably to a level of about 1 part per million weight as halogen or less, wherein the absorbent is preferably a metal compound, solid metal or molten metal, and (e) separating aromatic hydrocarbons and/or $C_{4+}$ non-aromatic hydrocarbons from the product mixture of step (d) to produce aromatic hydrocarbons and/or $C_{4+}$ non-aromatic hydrocarbons.

BRIEF DESCRIPTION OF THE DRAWING

FIG. 1 is a flow diagram illustrating the process of the present invention.

DETAILED DESCRIPTION OF THE INVENTION

The present invention provides an improved process for the production of aromatic compounds and/or $C_{4+}$ non-aromatic hydrocarbons from low molecular weight alkanes, primarily methane. Other alkanes, such as ethane, propane, butane, and pentane, may be mixed in with the methane. First, at least one low molecular weight alkane, preferably methane, is halogenated by reacting it with a halogen, preferably bromine. The monohaloalkane, preferably monobromomethane, which is produced thereby may be contacted with a suitable coupling catalyst which causes the monohaloalkane to react with itself to produce higher molecular weight hydrocarbons such as aromatics and/or $C_{4+}$ non-aromatic hydrocarbons and also a mixture of lower range molecular weight alkanes and likely some alkenes having 2 or 3 carbon atoms. A small amount of methane may also be produced. The aromatic compounds, such as benzene, toluene and xylenes, and/or the $C_{4+}$ non-aromatic hydrocarbons, may be separated from the methane and C$_{2-3}$ alkanes and alkenes. After an optional clean-up step to remove residual hydrogen bromide, the C$_{2-3}$ alkanes and alkenes or a portion thereof may be recycled to the bromination step or cracked in an alkane cracking system to produce ethylene and/or propylene. Higher molecular weight aromatic hydrocarbons may also be produced in the coupling step, such as those containing nine or more carbon atoms. These C$_{9+}$ aromatic hydrocarbons may be processed as described below and converted into olefins and/or more desirable aromatic hydrocarbons such as benzene, toluene and/or xylenes. Unfortunately, brominated organic impurities are also formed during this reaction.

The hydrocarbon feed may be comprised of a low molecular weight alkane. Low molecular weight alkanes include methane, ethane and propane, as well as butane and pentane. The preferred feed is natural gas which is comprised of methane and often contains smaller amounts of ethane, propane and other hydrocarbons. The most preferred feed is methane.

Higher molecular weight hydrocarbons are defined herein as those hydrocarbons having four or more carbon atoms. Higher molecular weight hydrocarbons include aromatic hydrocarbons, especially benzene, toluene and xylenes (hereinafter referred to as "BTX") and/or C$_{4+}$ non-aromatic hydrocarbons.

In a preferred embodiment, the coupling reaction may be carried out such that the production of aromatic hydrocarbons, specifically BTX, is maximized. The production of aromatic hydrocarbons may be achieved by the use of a suitable coupling catalyst under suitable operating conditions.

Representative halogens include bromine and chlorine. It is also contemplated that fluorine and iodine may be used but not necessarily with equivalent results. Some of the problems associated with fluorine possibly may be addressed by using dilute streams of fluorine. It is expected that more vigorous reaction conditions will be required for alkyl fluorides to couple and form higher molecular weight hydrocarbons. Similarly, problems associated with iodine (such as the endothermic nature of some iodine reactions) may likely be addressed by carrying out the halogenation and/or coupling reactions at higher temperatures and/or pressures. The use of bromine or chlorine is preferred and the use of bromine is most preferred. While the following description may only refer to bromine, bromination and/or bromomethanes, the description is applicable to the use of other halogens and halomethanes as well.

Bromination of the methane (methane will be used in the following description but other alkanes may be present as discussed above) may be carried out in an open pipe, a fixed bed reactor, a tube-and-shell reactor or another suitable reactor, preferably at a temperature and pressure where the bromination products and reactants are gases. Fast mixing between bromine and methane is preferred to help prevent over-bromination and coking. For example, the reaction pressure may be from about 100 to about 5000 kPa and the temperature may be from about 150 to about 600° C., more preferably from about 350 to about 550° C. and even more preferably from about 400 to about 515° C. Higher temperatures tend to favor coke formation and lower temperatures require larger reactors. Methane bromination may be initiated using heat or light with thermal means being preferred.

A halogenation catalyst may also be used. In an embodiment, the reactor may contain a halogenation catalyst such as a zeolite, amorphous alumino-silicate, acidic zirconia, tungstenates, solid phosphoric acids, metal oxides, mixed metal oxides, metal halides, mixed metal halides (the metal in such cases being for example nickel, copper, cerium, cobalt, etc.) and/or other catalysts as described in U.S. Pat. Nos. 3,935,289 and 4,971,664, each of which is herein incorporated by reference in its entirety. Specific catalysts include a metal bromide (for example, sodium bromide, potassium bromide, copper bromide, nickel bromide, magnesium bromide and calcium bromide), a metal oxide (for example, silicon dioxide, zirconium dioxide and aluminum trioxide) or metal (for example, platinum, palladium, ruthenium, iridium, gold, or rhodium) to help generate the desired brominated methane.

The bromination reaction product comprises monobromomethane, HBr and also small amounts of dibromomethane and tribromomethane. If desired, the HBr may be removed prior to coupling. The presence of large concentrations of the polybrominated species in the feed to the coupling reactor may decrease bromine efficiency and result in an undesirable increase in coke formation. In many applications, such as the production of aromatics and/or C$_{4+}$ non-aromatic hydrocarbons, it is desirable to feed only monobromomethane to the coupling reactor to improve the pconversion to the final higher molecular weight hydrocarbon products. In an of the invention, a separation step is added after the halogenation reactor in which the monobromomethane is separated from the other bromomethanes. The di- and tribromomethane species may be recycled to the bromination reactor. One separation method is described in U.S. Published Patent Application No. 2007/02388909, which is herein incorporated by reference in its entirety. Preferably, the separation is carried out by distillation. The di- and tribromomethanes are higher boiling than the monobromomethane, unreacted methane and HBr, which is also made by the bromination reaction:

$$CH_4 + Br_2 \rightarrow CH_3Br + HBr$$

In a preferred embodiment, the polybromomethanes may be recycled to the halogenation reaction and preferably reproportionated to convert them to monobromomethane. The polybromomethanes contain two or more bromine atoms per molecule. Reproportionation may be accomplished according to U.S. Published Patent Application 2007/0238909 which is herein incorporated by reference in its entirety. Reactive reproportionation is accomplished by allowing the methane feedstock and any recycled alkanes to react with the polybrominated methane species from the halogenation reactor, preferably in the substantial absence of molecular halogen. Reproportionation may be carried out in a separate reactor or in a region of the halogenation reactor.

The bromination and coupling reactions may be carried out in separate reactors or the process may be carried out in an integrated reactor, for example, in a zone reactor as described in U.S. Pat. No. 6,525,230 which is herein incorporated by reference in its entirety. In this case, halogenation of methane may occur within one zone of the reactor and may be followed by a coupling step in which the liberated hydrobromic acid may be adsorbed within the material that catalyzes condensation of the halogenated hydrocarbon. Hydrocarbon coupling may take place within this zone of the reactor and may yield the product higher molecular weight hydrocarbons including aromatic hydrocarbons. It is preferred that separate reactors be used for bromination and coupling because operating conditions may be optimized for the individual steps and this allows for the possibility of removing polybrominated-methane before the coupling step.

Coupling of monobromomethane may be carried out in a fixed bed, fluidized bed or other suitable reactor. The temperature may range from about 150 to about 600° C., preferably from about 300 to about 550° C., most preferably from about 350 to about 475° C., and the pressure may range from about 10 to about 3500 kPa absolute, preferably about 100 to about 2500 kPa absolute. In general, a relatively long residence time favors conversion of reactants to products as well as product selectivity to BTX and/or $C_{4+}$ non-aromatic hydrocarbons, while a short residence time means higher throughput and possibly improved economics. It is possible to change product selectivity by changing the catalyst, altering the reaction temperature, pressure and/or altering the residence time in the reactor. Low molecular weight alkanes may also exit the coupling reactor. These low molecular weight alkanes may be comprised of ethane and propane but may also include methane and a small amount of $C_{2-3}$ alkenes. Some of these may be recycled to the bromination reactor or the low molecular weight alkanes may be directed to a cracking step.

Preferred coupling catalysts for use in the present invention are described in U.S. Patent Application No. 2007/0238909 and U.S. Pat. No. 7,244,867, each of which is herein incorporated by reference in its entirety.

A metal-oxygen cataloreactant may also be used to facilitate the coupling reaction. The term "metal-oxygen cataloreactant" is used herein to a cataloreactant material containing both metal and oxygen. Such cataloreactants are described in detail in U.S. Published Patent Application Nos. 2005/0038310 and 2005/0171393 which are herein incorporated by reference in their entirety. Examples of metal-oxygen cataloreactants given therein include zeolites, doped zeolites, metal oxides, metal oxide-impregnated zeolites and mixtures thereof. Nonlimiting examples of dopants include alkaline earth metals, such as calcium, magnesium, manganese and barium and their oxides and/or hydroxides.

Hydrogen bromide may also be produced along with monobromomethane in the bromination reactor. The hydrogen bromide may be carried over to the coupling reactor or, if desired, may be separated before coupling. The products of the coupling reaction may include higher molecular weight hydrocarbons, especially BTX and/or $C_{4+}$ non-aromatic hydrocarbons. In a preferred embodiment, the hydrogen bromide may be separated from the higher molecular weight hydrocarbon products by distillation.

The coupling reaction product higher molecular weight hydrocarbons and hydrogen bromide may be sent to an absorption column wherein the hydrogen bromide may be absorbed in water using a packed column or other contacting device. Input water in the product stream may be contacted either in co-current or countercurrent flow with countercurrent flow preferred for its improved efficiency. One method for removing the hydrogen bromide from the higher molecular weight hydrocarbon reaction product is described in U.S. Pat. No. 7,244,867 which is herein incorporated by reference in its entirety. HBr present in the $C_{2-3}$ alkanes and alkenes stream or the product stream from the bromination reactor may also be removed therefrom by this method.

In an embodiment, the hydrogen bromide is recovered by displacement as a gas from its aqueous solution in the presence of an electrolyte that shares a common ion or an ion that has a higher hydration energy than hydrogen bromide. Also aqueous solutions of metal bromides such as calcium bromide, magnesium bromide, sodium bromide, potassium bromide, etc. may be used as extractive agents.

In another embodiment, catalytic halogen generation is carried out by reacting hydrogen bromide and molecular oxygen over a suitable catalyst. The oxygen source may be air, pure oxygen or enriched air. A number of materials have been identified as halogen generation catalysts. It is possible to use oxides, halides, and/or oxyhalides of one or more metals, such as magnesium, calcium, barium, chromium, manganese, iron, cobalt, nickel, copper, zinc, etc. After the HBr is separated from the hydrocarbon products, it may be reacted to produce bromine for recycle to the bromination step. Catalysts and methods for regeneration of the bromine are described in detail in U.S. Published Application 2007/0238909 which is herein incorporated by reference in its entirety. Recovery of bromine is also described therein.

In addition to the higher molecular weight hydrocarbons and the hydrogen bromide, other materials may exit from the coupling reactor. These include methane, light ends ($C_{2-3}$ alkanes and alkenes) and heavy ends (aromatic $C_{9+}$ hydrocarbons. The methane may be separated from these other materials (e.g., by distillation) and recycled to the bromination reactor. The $C_{2-3}$ alkanes, and optionally the alkenes, may optionally be separated from the other materials and introduced into an alkane cracker which produces ethylene and/or propylene. The $C_{2-3}$ alkanes and alkenes stream may contain some HBr which may be removed prior to cracking. The $C_{9+}$ aromatic hydrocarbons may be hydrogenated. The hydrogen for hydrogenation may be that produced in the alkane cracker. The resulting hydrogenated $C_{9+}$ stream may be cracked in a conventional cracker to produce additional olefins and/or aromatic hydrocarbons. Alternatively, the $C_{9+}$ aromatic hydrocarbons may be converted to xylenes by reproportionation with toluene, hydrodealkylated to BTX or they may be upgraded by a combination of these two steps.

The present invention provides an integrated process for producing aromatic hydrocarbons and/or $C_{4+}$ non-aromatic hydrocarbons from low molecular weight alkanes, preferably methane, which comprises:

(a) contacting one or more low molecular weight alkanes, preferably methane, with a halogen, preferably bromine, under process conditions sufficient to produce a monohaloalkane, preferably monobromomethane, (b) reacting the monohaloalkane in the presence of a coupling catalyst to produce a stream comprising aromatic hydrocarbons and/or $C_{4+}$ non-aromatic hydrocarbons and halogenated organic impurities, (c) hydrotreating the stream from step (b) under conditions sufficient to convert most of said impurities to hydrogen halide, preferably hydrogen bromide (HBr), and hydrocarbons while minimizing the hydrogenation of the aromatic hydrocarbons and/or $C_{4+}$ non-aromatic hydrocarbons, to produce a stream comprising aromatic hydrocarbons and/or $C_{4+}$ non-aromatic hydrocarbons and refractory halogenated organic impurities, (d) contacting the stream from step (c) with a purification absorbent capable of reducing the quantity of said refractory halogenated organic impurities in said stream, preferably to a level of not more than about 1 part per million as bromine, wherein the absorbent is preferably a metal compound, solid metal or molten metal, and (e) separating aromatic hydrocarbons and/or $C_{4+}$ non-aromatic hydrocarbons from the product mixture of step (d) to produce aromatic hydrocarbons and/or $C_{4+}$ non-aromatic hydrocarbons.

In this invention, the brominated organic impurities which contaminate various hydrocarbon streams in a process for producing aromatic hydrocarbons and/or C4+ non-aromatic hydrocarbons by bromination of methane and coupling of monobromomethane are converted to hydrocarbons by a two-step process.

In the first step, hydrotreating by added hydrogen in the presence of an appropriate catalyst, the majority of the organo-bromides are converted to hydrocarbons and HBr. Appropriate catalysts for the hydrotreating step include, but are not limited to, Pd, Pt, Ir, Ru and Rh on acceptable support materials including carbon, silica, alpha-alumina, gamma-alumina, zirconia and titania, preferably with surface areas ranging from 1 to 300 square meters per gram. Temperature and pressures can be varied over a wide range, typically from 50° C. to 250° C. and 50 psig to 1000 psig, respectively. Temperature, pressure, and residence time are adjusted to obtain a near complete conversion of the organo-bromides without significantly hydrogenating the aromatics into saturated hydrocarbons. The reaction can be conducted in liquid phase or vapor phase. HBr is removed after the hydrotreating step to produce a hydrotreating product stream.

The hydrotreating step generally may reduce the amount of organobromides from about 0.5-5% wt to about 10-1000 parts per million weight as bromine.

This is then followed by contacting the hydrotreated product stream which contains the refractory brominated organic impurities with a purification absorbent capable of reducing the quantity of said refractory brominated organic impurities in said stream, preferably by passing the hydrocarbon stream over a molten metal or metal on a fixed bed. An essentially complete removal of the refractory bromides is achieved in the absorbent step without substantially affecting the purity of the hydrocarbons. Metals such as Li, Na, K, Na/K, Ca, Mg, Cr, Mn, Co, Ni, Cu, Zn, Fe, Ag or their oxides, nitrates, carbonates, or other salts in pure form or supported on refractory carrier materials, can be used for the absorption process.

The absorption step is preferably carried out with the absorbent held in a fixed bed. The hydrotreating product stream can be passed over the absorbent in liquid form (under sufficient temperature and required pressure) or as a vapor.

The absorption step reduces the amount of organobromides from about 10-1000 parts per million weight as bromine to about 0.01-1 parts per million weight as bromine.

Heat from the conversion of methane to aromatics and/or other heavy hydrocarbons, including heat generated in the generation of bromine, may be used in the process to supply energy required in alkane cracking, heating the feed streams for the bromination, reproportionation and/or coupling reactions and for heat required in any of the fractionation operations. At least part of the energy released in the conversion of hydrogen bromide to bromine may be recovered and utilized in steps (a)-(d) or any combination thereof and optionally in upstream (including but not limited to gas feedstock processing) and/or downstream processing (including, but not limited to BTX conversion and purification, disproportion reactions, aromatic $C_{9+}$ hydrocarbon reproportionation reactions, isomerization reactions, and conversion of BTX to downstream products).

One of the invention is illustrated in FIG. 1. Methane derived from natural gas purification is delivered through line 1 to the bromination reactor 100 at 30 barg (3000 kPag) and ambient temperature. The methane stream is combined with recycle methane stream 2, heated to 450° C., and fed to the bromination reactor 100. Bromine liquid is pumped from storage in line 3, vaporized and heated to 250° C., and fed in a staged manner into to the bromination reactor 100.

In the bromination reactor 100, bromine reacts adiabatically with methane to form methyl bromide, methyl dibromide, methyl tribromide, and hydrogen bromide. In this example, the reactor does not utilize a catalyst. During normal operation, a small amount of coke is produced. The bromination reactor 100 is comprised of at least 2 parallel reactor trains to allow for one train to be decoked while the other train(s) remains in normal operation. Reactor effluent gas from the decoking operation is routed through line 4 to the bromine generation reactor 110 (described below).

A gas mixture containing methyl bromides, hydrogen bromide and unreacted methane, exits the bromination reactor 100 through line 5 at 510° C. and 30 barg (3000 kPag) and enters the reproportionation reactor 120. The reproportionation product gas stream 7 is cooled and fractionated in a conventional distillation column 130 to separate polybromides from the other reproportionation products. Polybrominated hydrocarbons, recovered from distillation column 130, are fed to the reproportionation reactor 120 through line 6 where di- and tri-substituted methyl bromide and other polybrominated hydrocarbons react adiabatically with unreacted methane to form monobromomethane. In this example, the reproportionation reactor 120 does not utilize a catalyst.

The remaining components of the reproportionation product stream 7 (primarily monobromomethane, hydrogen bromide, and unreacted methane) are recovered as a separate stream 8, vaporized, reheated to 400° C., and fed to the coupling reactor 140.

In the coupling reactor 140, monobromomethane reacts adiabatically over a manganese-based catalyst at a temperature of 425° C. and 25 barg (2500 kPag) to produce a mixture of compounds comprised predominately of benzene, toluene, xylenes, and/or $C_{4+}$ non-aromatic hydrocarbons, and ethane and propane. The coupling reactor 140 is comprised of multiple fixed bed catalytic reactors operating on a reaction/regeneration cycle. During the reaction phase, monobromomethane reacts to form mixed products. At the same time, coke is formed and gradually deactivates the catalyst. During the regeneration phase of a reactor, reactor feed is redirected to one of the reactors vessels which is in the reaction phase of the cycle. Heated air is utilized to burn coke and regenerate the catalyst. Reactor effluent gas is routed through line 9 to the bromine generation reactor 110.

Product gas from the coupling reactor 140 is directed through line 10 and cooled and fractionated in conventional distillation column 160 to produce two streams. The higher boiling stream, 11, is comprised primarily of benzene, toluene, and xylenes. The lower boiling stream, 18, is comprised primarily of methane, ethane, propane, butanes, pentanes, and hydrogen bromide. The split of material between streams 11 and 18 is adjusted such that the majority of the methyl bromide present in the feed to column 160 is sent with stream 11.

The higher boiling stream 11 from distillation column 160 is heated and routed to hydrotreater 170. Hydrogen from line 28 is added to this adiabatic trickle phase reactor which uses a palladium-based catalyst to convert the organobromide impurities to the equivalent hydrocarbons and hydrogen bromide.

Stream 13 exiting the hydrotreater 170 is fractionated in conventional distillation column 180 to recover product stream 14A which is comprised primarily of benzene, toluene, and xylenes (BTX) and/or $C_{4+}$ non-aromatic hydrocarbons, but containing trace amounts of the refractory organobromides, and a second lights stream 40 which is comprised primarily of hydrogen bromide, unreacted hydrogen, and light hydrocarbons (produced by hydrogenolysis or the organobromide impurities in the hydrotreater 170).

Product stream 14A containing the refractory organobromides is passed over a silver-based catalyst, which acts as the purification absorbent, held in guardbed reactor 185. Bromine from the refractory organobromides is retained on the absorbent. Purified product stream 14B leaving guardbed reactor 185 is essentially bromine-free.

Purified product stream 14B is combined with a $C_{6+}$ stream 15 generated by steam cracking (described below) and fed to conventional distillation column 190 to produce benzene in stream 111. The non-benzene fraction from column 190, comprised of toluene and mixed xylenes, is fed through line 112 to a conventional disproportionation unit 200 to produce roughly eqimolar benzene and xylenes in line 113 which are separated in separator 210. The benzene stream 114 is combined with the product benzene stream 111 to form benzene product stream 16 (or optionally fed to column 180 if additional purification is required). The mixed xylenes are converted to para-xylene via conventional technology (Perex—recovering the para-xylene from the xylene mixture, followed by re-isomerization of the para-isomer-deprived mixed xylenes to an equilibrium mixture, and repeating the cycle of recovery and isomerization) and leave as product stream 17. Light and heavy ends from benzene purification, disproportionation, and xylenes conversion and distillation are used in the process as fuel or recycled (e.g. as feed to the steam cracker). Benzene and para-xylene are stored and sold as products.

The lower boiling stream 18 from column 160 is comprised of hydrogen bromide and $C_{1-3}$ hydrocarbons, primarily alkanes. This stream 18 is fractionated in distillation column 220 to produce a stream 19 that is comprised primarily of $C_1$ and $C_2$ hydrocarbons, primarily methane and ethane and a second stream 20 that is comprised of hydrogen bromide and $C_{3-5+}$ hydrocarbons (primarily propane, butanes, and pentanes). The $C_1$ and $C_2$ hydrocarbon stream 19 is fractionated in column 240 to produce methane, which is recycled to bromination reactor 100 through line 21, and an ethane/ethylene stream 22. The second stream 20 is fractionated in column 250 to produce a tops stream 23 containing hydrogen bromide, which is routed to bromine generation reactor 110, and a bottoms stream 24 containing $C_{3-5+}$ hydrocarbons.

The $C_{3-5+}$ hydrocarbon stream 24 is combined with ethane/ethylene stream 22 and lights stream 40 and sent to water scrubber 260 to remove small residual amounts of hydrogen bromide. Hydrogen bromide is recovered in line 26 and sent to bromine generation reactor 110. The combined $C_{2-5+}$ mixed hydrocarbon fraction 25 is fed to steam cracker 270.

Steam cracker 270 uses conventional furnace technology to crack the mixed hydrocarbon feed 25 to produce primarily ethylene, propylene, hydrogen, methane, butylene, $C_{5s}$, benzene, and other $C_{6s}$ in line 27. Downstream of the furnaces, standard cracker product separation technology is employed to separate hydrogen 28 for use in the hydrotreater 170 and for export through line 29 and/or for an optional hydro-dealkylation reactor (not shown) if that technology is used to convert toluene into benzene.

The standard cracker product separation technology employed herein comprises the separation of methane and hydrogen from $C_{2-5+}$ hydrocarbons in column 280. Methane and hydrogen are directed to column 290 through line 40. Methane is separated from hydrogen in column 290. Methane in line 33 is recycled to bromination reactor 100.

$C_{2-5+}$ hydrocarbons are fractionated in fractionator 300 to produce $C_{4-5}$ fraction 34 which is recycled to coupling reactor 140, $C_{6+}$ fraction 15 which is routed to BTX fractionation 190 and ethylene and propylene which are separated, purified, and exported as products, ethylene in line 31 and propylene in line 32.

Hydrogen bromide in line 23 from column 250 and in line 26 from scrubber 260 is combined in line 35 and is heated and fed to the bromine generation reactor 110. Air is compressed and fed through line 36 to bromine generation reactor 110 and the catalyst is continuously regenerated. Regeneration gas from coupling reactor 140 (line 9) and bromination reactor decoker 4 is also fed to bromine generation reactor 110. Bromine generation reactor 110 is comprised of several shell/tube exchangers whose tubes are filled with copper oxide catalyst. Heat released by the exothermic conversion of hydrogen bromide to bromine is removed by generation of steam (line 37) and may be subsequently utilized elsewhere in the process (e.g. in the fractionation steps). The effluent from reactor 110 is further cooled, generating additional steam.

The inert gases, primarily nitrogen and unreacted oxygen are routed to a bromine scavenging adsorbent (not shown) and then released through line 38. The liquid product from bromine generation reactor 110, comprised of water and bromine, is phase separated at sub-ambient temperature and then distilled to produce a water stream 39 and a bromine stream 3 which is dried and recycled to bromination reactor 100. The water stream 39 is further purified and released.

EXAMPLE 1

Referring to FIG. 1, the flow rate in methane feed line 1 to the bromination reactor 100 is 100 kg/hr, the flow rate in methane recycle line 2 is 73 kg/hr and the flow rate in the bromine feed line 3 is 1164 kg/hr. Reactor 100 is operated at 510° C. and 3000 kPa. The conversion of methane is 50% and the selectivity to monobromomethane is 67%.

Reproportionation reactor 120 is also operated at 510° C. and 3000 kPa. The conversion is 43% and the selectivity to monobromomethane is 100%. Coupling reactor 140 is operated at 425° C. and 2500 kPa. The conversion of the monobromomethane is 100% and the selectivity to BTX is 32%.

The hydrocarbon stream from reactor 140 is sent to hydrotreater 170 wherein the 0.5 to 5% wt organobromide concentration in the feed is reduced to 10 to 1000 ppm wt. The guardbed reactor 185 containing a silver-based catalyst (the purification absorbent) is positioned at downstream of the hydrotreater 170 and distillation column 180. The guardbed rector removes the refractory organobromides from the BTX stream down to a concentration of 1 ppm wt (as bromine) or less.

Bromine generation reactor 110 is operated at 375° C. and 200 kPa and the flow rate of air through feed line 36 is 554 kg/hr. The conversion and selectivity are both 100%. The flow rate in water stream 39 is 131 kg/hr.

Steam cracker 270 is operated at 840° C. and 100 kPa. The conversion of the monobromomethane is 84% and the selectivity to lower olefins is 60%.

14 kg/hr of benzene and 23 kg/hr of p-xylene are produced. 25 kg/hr of ethylene and 12 kg/hr of propylene are produced.

EXAMPLE 2

Purification Absorbent materials for the guardbed reactor 185 were evaluated by using a gas feed consisting of methyl bromide in nitrogen. Several materials were used but the one which performed the best was a material comprised of silver and potassium supported on alumina. The guard beds were placed in a nitrogen stream that contained from 120 to 10,000 ppmv methyl bromide (pressure=1 atm, T=170° C., GHSV=from 980 to 16,000 hr−1).

The experiments were carried out in a microreactor to which was delivered controlled flowrates of "stock methyl bromide" diluted with pure N2 to achieve the desired MeBr concentration (1% v MeBr, balance N2). The outlet line led to an auxiliary gas chromatograph that was configured to measure very low levels of organic halides (sampling τ=30 min). A description of the GC configuration is provided in Table 1. The instrument was first calibrated for measuring methyl bromide delivered over the range 0-12,000 ppmv (Experiment 1) or 0-1200 ppmv (Experiments 2-5), with primary emphasis placed on accurate measurement and sensitivity in the low-ppm range. Once experiments began, methyl bromide levels in the outlet stream were recorded twice per hour.

The following guard bed materials were evaluated:

A. "Ag/K/Al2O3"—this material was prepared by aqueous silver nitrate plus potassium nitrate vacuum impregnation onto 1.3 mm trilobe Criterion alumina extrudates (S.A=100-150 m2/g), followed by centrifugation for 2 minutes at 200 rpm and drying in a shaking basket for 10 minutes at 170° C.

The dried material was then calcined in air for 15 minutes at 250° C. Elemental analysis indicates that the final material contained 23.4% w Ag and 2.72% w K.

B. "Cu/Al2O3"—KL-5715 catalyst made by KataLeuna which consists of 10% w CuO on alumina.

C. "Cu/Zn/Al2O3"—KL-4211 catalyst catalyst made by KataLeuna which has a bulk composition of 48% w CuO/36% w ZnO/16% w Al2O3.

In Experiment 1, guard bed material Ag/K/Al2O3 was crushed and sieved to 30-40 mesh size. 1.00 g material was loaded into a U-shaped stainless steel microreactor tube (0.25" OD, 0.18" ID) and the crushed material was secured in place with small glass wool plugs. The tube was placed in the liquid metal temperature control bath and affixed to the feed delivery and exit systems. As feedstock flow was initiated, data collection via the auxiliary GC commenced. Data collection continued until at least 50% breakthrough was observed, which is to say, until the concentration of methyl bromide in the outlet stream reached at least 50% of the level being fed. The net amount of bromine sorbed per time interval was calculated by multiplying the amount of bromine fed per period times the fraction of methyl bromide that was not observed in the outlet stream.

Experiments 2-5 were conducted in like manner. In Experiment 2, the concentration and space velocity of the bromide stream was varied several times during the run. In Experiments 3-5, MeBr concentration and space velocity remained constant throughout. Complete descriptions of the experimental conditions are given in Table 1.

The experimental results are summarized in Table 1. Guard bed sorption effectiveness was rated by comparing cumulative sorption at the point where "% breakthrough" had reached 20% (BT-20%). At BT-20%, the GC detects a concentration of methyl bromide exiting the guard bed that is equal to 20% of the inlet concentration—Elemental Bromine Absorbed (as % w of Guard Bed Mass). For example, a value of 20% means that each gram of guard bed material has sorbed 0.2 g bromine.

The very high bromide concentration combined with high space velocity used in Experiment 1 immediately overwhelmed the bed, resulting in essentially full breakthrough even in the first sampling interval.

For Experiment 2, both the concentration and the space velocity were reduced. With a few mid-course modifications, "100% breakthrough" was achieved in about a week. At the point of BT-20%, it was calculated (basis summation of point-by-point sorption) that the bed had sorbed an amount of methyl bromide equivalent to 14.3% w of its mass.

Experiment 3 utilized the highest flowrate (325 cc/min=GHSV 3200 hr−1) and the highest bromide concentration (1100 ppmv) from Experiment 2 but was conducted at a much lower temperature (170° C. vs. 250° C. in Experiment 2). Counterintuitively (for a presumably chemisorption phenomenon), the lower temperature was significantly more effective for bromine capture when using the Ag/K/Al2O3 guard bed material which sorbed 24.8% of its weight in bromine by the time BT-20% was reached.

To confirm the impressive results of this experiment, the spent bed material was submitted for bromine analysis by x-ray fluorescence. The spent bromine-loaded material contained 21.9% w bromine, which corresponds to 28.0% w bromine basis the original 5.0 g mass of the guard bed. By the time methyl bromide flow ceased in Experiment 3, it was calculated (by summing all of the bromine absorbed for each sampling interval) that the bed had sorbed 25.6% w bromine basis the original 5.0 g mass of the guard bed. Given the challenge of metering low levels of methyl bromide to the bed and accurately measuring even lower levels exiting the bed, the calculated 25.6% w value is considered to be in very good agreement with the analytical 28.0% w value.

Experiments 4 and 5 measured the methyl bromide sorption capacity of the selected copper-based and copper-zinc-based materials, using the same conditions as Experiment 3. Neither of the copper-containing materials was as effective as silver on alumina but the copper/alumina material performed reasonably well.

TABLE 1

Interception of Methyl Bromide from MeBr/N$_2$ Stream

| Experiment | Guard Bed | GB Mass (g) | Bed Temp (° C.) | Flowrate (cc/min) | GHSV (hr$^{-1}$) | [MeBr] (ppmv) | BT-20% (g Br per 100 g GB) |
|---|---|---|---|---|---|---|---|
| #1 | Ag/K/Al$_2$O$_3$ | 1.0 | 250 | 325 | 16,000 | 10,000 | ~0 |
| #2 | Ag/K/Al$_2$O$_3$ | 5.0 | 250 | 100/ 325/ 100 | 980/ 3200/ 980 | 120/ 120/ 1100 | 14.3 |
| #3 | Ag/K/Al$_2$O$_3$ | 5.0 | 170 | 325 | 3200 | 1100 | 24.8 |
| #4 | Cu/Al$_2$O$_3$ | 5.0 | 170 | 325 | 3200 | 1100 | 6.5 |
| #5 | Cu/Zn/Al$_2$O$_3$ | 5.0 | 170 | 325 | 3200 | 1090 | 0.3 |

Agilent 6890 Gas Chromatograph fitted with heated valve box (80° C.) containing 3 Valco valves for stream selection, sample stream isolation and sample injection.
Agilent GasPro 60 m × 0.32 mm part #113-4362 column with helium carrier flow of 3.5 ml/min (velocity 44 cm/sec) in the constant flow mode.
Inlet temperature 250° C.; Purge flow = 3.5 ml/min; Oven temperature 250° C.; FID detector.

EXAMPLE 3

The results shown below demonstrate the feasibility of using Na metal as the purification absorbent for the removal of organobromides. The experiments were conducted at room temperature by batch-contacting a toluene/xylene mixture containing known amounts of 1-bromo-heptane and 2-bromo-mesitylene as model compounds with sodium metal provided in the form of a solution. The sodium reagent, Na-biphenyl, was purchased from Aldrich Chemical Company.

Test results with Na metal: Using 2-bromo-mesitylene and 1-bromo-heptane as test compounds in a mixture of toluene and xylene, the effectiveness of sodium metal was tested at room temperature. The reduction of the organo-bromides was complete in 5 minutes or less as determined by GC analysis of the reaction mixture. The "others" shown in the tables below are predominantly from the Na-biphenyl reagent.

TABLE 2

Debromination of 2-Bromomesitylene in Toluene/Xylene Mixture with Na-Biphenyl (Weight % Results)

| Sample (Rxn Time, min) | Toluene | p-Xylene | Mesitylene | 1Br-C7 | 2Br-Mesitylene | Others |
|---|---|---|---|---|---|---|
| Feed, 2-1 (0) | 53.50 | 45.91 | 0.00 | 0.02 | 0.47 | 0.09 |
| Prod, 2-3 (5) | 50.70 | 43.49 | 0.26 | 0.00 | 0.00 | 5.54 |
| Prod, 2-4 (10) | 50.68 | 43.52 | 0.26 | 0.00 | 0.00 | 5.54 |
| Prod, 2-5 (15) | 50.68 | 43.55 | 0.26 | 0.00 | 0.00 | 5.51 |

TABLE 3

Debromination of 1-Bromoheptane in Toluene/Xylene Mixture with Na-Biphenyl (Weight % Results)

| Sample (Rxn Time, min) | Toluene | p-Xylene | 1Br—C7 | Others |
|---|---|---|---|---|
| Feed, 2-2 (0) | 59.60 | 39.97 | 0.33 | 0.10 |
| Prod, 3-1 (5) | 53.36 | 35.77 | 0.01 | 10.86 |
| Prod, 3-2 (10) | 53.42 | 35.83 | 0.01 | 10.75 |

Test Results with Zn dust: Using 1-bromo-heptane as test compound in a mixture of toluene and xylene, the effectiveness of zinc in the form of a powder was tested at the reflux temperature of the solution. No reduction of the organobromide was observed under these conditions. It is believed that higher temperatures are required to effect the reaction. After removing the 12.5 hour sample, ethylene glycol was added and the heating continued for another 4.0 hours before obtaining the last sample.

TABLE 4

Debromination of 1-Bromoheptane with Zinc Dust (Weight % Results)

| Sample (Rxn Time, Hour) | Toluene | p-Xylene | 1Br—C7 | Others |
|---|---|---|---|---|
| Feed, 2-2 (0) | 59.61 | 39.98 | 0.33 | 0.08 |
| Prod, 4-1 (1.75) | 58.99 | 40.59 | 0.34 | 0.08 |
| Prod, 4-2 (12.5) | 54.95 | 44.56 | 0.40 | 0.09 |
| Prod, 4-3 (16.5) | 53.87 | 45.65 | 0.38 | 0.09 |

What is claimed is:

1. An integrated process for producing aromatic hydrocarbons and/or $C_{4+}$ non-aromatic hydrocarbons from low molecular weight alkanes, preferably methane, which comprises:
   (a) contacting one or more low molecular weight alkanes, preferably methane, with a halogen under process conditions sufficient to produce a monohaloalkane, preferably monobromomethane,
   (b) reacting the monohaloalkane in the presence of a coupling catalyst to produce a stream comprising aromatic hydrocarbons and/or $C_{4+}$ non-aromatic hydrocarbons and halogenated organic impurities,
   (c) hydrotreating the stream from step (b) under conditions sufficient to convert most of said impurities to hydrogen halide and hydrocarbons while minimizing the hydrogenation of the aromatic hydrocarbons, to produce a stream comprising aromatic hydrocarbons and refractory halogenated organic impurities,
   (d) contacting the stream from step (c) with a purification absorbent capable of reducing the quantity of said refractory halogenated organic impurities in said stream from (c) to a level of 1 part per million weight as halogen or less, wherein the absorbent is a metal compound, solid metal or molten metal, and
   (e) separating aromatic hydrocarbons and/or $C_{4+}$ non-aromatic hydrocarbons from the product mixture of step (d) to produce aromatic hydrocarbons and/or $C_{4+}$ non-aromatic hydrocarbons.

2. The process of claim 1 wherein the low molecular weight alkanes is methane.

3. The process of claim 1 wherein the halogen is bromine.

4. The process of claim 1 wherein the monohaloalkane is monobromomethane.

5. The process of claim 1 wherein the hydrogen halide is hydrogen bromide.

6. The process of claim 1 wherein the low molecular weight alkanes come from natural gas.

7. The process of claim 1 wherein the catalyst for the hydrotreating step is selected from the group consisting of Pd, Pt, Ir, Ru and Rh on acceptable support materials including carbon, silica, alpha-alumina, gamma-alumina, zirconia and titania, with surface areas ranging from 1 to 300 square meters per gram.

8. The process of claim 1 wherein the purification absorbent is selected from the group consisting of Li, Na, K, Na/K, Ca, Mg, Cr, Mn, Co, Ni, Cu, Zn, Fe, Ag or their oxides, nitrates, carbonates, or other salts in pure form or supported on refractory carrier materials.

\* \* \* \* \*